United States Patent
Satake et al.

(10) Patent No.: US 9,833,132 B2
(45) Date of Patent: Dec. 5, 2017

(54) IMAGING UNIT AND IMAGING MODULE

(71) Applicants: OLYMPUS CORPORATION, Tokyo (JP); OLYMPUS MEDICAL SYSTEMS CORP., Tokyo (JP)

(72) Inventors: Nau Satake, Yokohama (JP); Tsutomu Sasamoto, Hino (JP)

(73) Assignee: OLYMPUS CORPORATION, Tokyo (JP)

(*) Notice: Subject to any disclaimer, the term of this patent is extended or adjusted under 35 U.S.C. 154(b) by 319 days.

(21) Appl. No.: 14/271,686

(22) Filed: May 7, 2014

(65) Prior Publication Data
US 2014/0240476 A1    Aug. 28, 2014

Related U.S. Application Data

(63) Continuation of application No. PCT/JP2012/066998, filed on Jul. 3, 2012.

(30) Foreign Application Priority Data

Nov. 9, 2011 (JP) ................................ 2011-245854

(51) Int. Cl.
*A61B 1/05* (2006.01)
*A61B 1/00* (2006.01)
(Continued)

(52) U.S. Cl.
CPC ............ *A61B 1/05* (2013.01); *A61B 1/00096* (2013.01); *A61B 1/00101* (2013.01);
(Continued)

(58) Field of Classification Search
CPC combination set(s) only.
See application file for complete search history.

(56) References Cited

U.S. PATENT DOCUMENTS

| 4,890,159 A | 12/1989 | Ogiu | |
|---|---|---|---|
| 2008/0262309 A1* | 10/2008 | Miyoshi | A61B 1/0052 600/146 |
| 2010/0085466 A1* | 4/2010 | Fujimori | A61B 1/00096 348/340 |

FOREIGN PATENT DOCUMENTS

| EP | 2 687 144 A1 | 1/2014 |
|---|---|---|
| JP | 63-124495 A | 5/1988 |

(Continued)

OTHER PUBLICATIONS

Extended Supplementary European Search Report dated May 21, 2015 from related European Application No. 12 84 7981.3.
(Continued)

*Primary Examiner* — Sath V Perungavoor
*Assistant Examiner* — Janese Duley
(74) *Attorney, Agent, or Firm* — Scully, Scott, Murphy & Presser, P.C.

(57) ABSTRACT

An imaging unit includes: a columnar optical member including an incident surface on which light is incident, a reflecting surface for reflecting the light incident from the incident surface in a direction different from the incident surface, and an emission surface for causing the light incident from a direction orthogonal to the incident surface and reflected from the reflecting surface to travel in a straight line and emitting the light to the outside; an imaging device including a light receiving unit, formed on a surface of the imaging device, for receiving the light emitted from the emission surface and performing photoelectric conversion on the light; and a cylindrical imaging holder, protruding from at least part of an outer edge of one end in line with a side surface shape of the optical member, for defining the position of the incident surface and holding the optical member.

7 Claims, 13 Drawing Sheets

(51) Int. Cl.
*G02B 23/24* (2006.01)
*H04N 5/225* (2006.01)

(52) U.S. Cl.
CPC .......... *A61B 1/051* (2013.01); *G02B 23/2484* (2013.01); *H04N 5/2252* (2013.01); *H04N 5/2253* (2013.01); *H04N 5/2254* (2013.01)

(56) References Cited

FOREIGN PATENT DOCUMENTS

| | | | |
|---|---|---|---|
| JP | 1-201229 A | 8/1989 |
| JP | 8/106055 A | 4/1996 |
| JP | 2006-91406 A | 4/2006 |
| JP | 2009-273642 A | 11/2009 |
| WO | 2011/058912 A1 | 5/2011 |
| WO | 2011/092901 A1 | 8/2011 |

OTHER PUBLICATIONS

International Search Report dated Sep. 18, 2012 from related International Application No. PCT/JP2012/066998.

* cited by examiner

IMAGING UNIT AND IMAGING MODULE

CROSS-REFERENCE TO RELATED APPLICATIONS

This application is a continuation of PCT international application Ser. No. PCT/JP2012/066998 filed on Jul. 3, 2012 which designates the United States based upon and claims the benefit of priority from Japanese Patent Application No. 2011-245854, filed on Nov. 9, 2011, the entire contents of which are incorporated herein by reference.

BACKGROUND OF THE INVENTION

1. Field of the Invention

The present invention relates to an imaging unit and imaging module that include an imaging device and an optical member.

2. Description of the Related Art

Conventionally, electronic imaging modules supporting various types from a digital camera and a digital video camera to a mobile phone with an imaging function and to an endoscope system for observing the inside of an organ of a subject have appeared. Among them, the endoscope system includes an imaging unit where an imaging device is implemented on a distal end section of a slim and long insertion tool having flexibility. The insertion tool is inserted into the body cavity to perform things such as observing a region to be examined.

The imaging unit includes the imaging device such as a CCD image sensor or a CMOS image sensor, forms an optical image of an object on a light receiving unit of the imaging device by an optical system such as a lens, and captures the image data of the object by an photoelectric conversion process of the imaging device.

Conventionally the endoscope apparatus has been required to downsize the diameter of the distal end section of the insertion tool to reduce a burden on the subject. In recent years, an imaging unit was proposed where a prism is mounted on an imaging device placed substantially parallel to the optical axis of an objective lens system so as to ensure a sufficient light receiving area on the imaging device even if the area of a vertical plane with respect to the optical axis, the area being available for the imaging unit, is reduced due to the downsizing of the diameter of the distal end section of the insertion tool (see, for example, Japanese Laid-open Patent Publication No. 8-106055).

SUMMARY OF THE INVENTION

An imaging unit according to one aspect of the present invention includes: a columnar optical member having a substantially circular shape when viewed from a light incident direction, the optical member including an incident surface on which light is incident, a reflecting surface for reflecting the light incident from the incident surface in a direction different from the incident surface, and an emission surface for causing the light incident from a direction orthogonal to the incident surface and reflected from the reflecting surface to travel in a straight line and emitting the light to the outside; an imaging device including a light receiving unit, formed on a surface of the imaging device, for receiving the light emitted from the emission surface and performing photoelectric conversion on the light; and a cylindrical imaging holder, protruding from at least part of an outer edge of one end in line with a side surface shape of the optical member, for defining the position of the incident surface and holding the optical member.

An imaging module according to another aspect of the present invention includes: an imaging unit including a columnar optical member having a substantially circular shape when viewed from a light incident direction, the optical member including an incident surface on which light is incident, a reflecting surface for reflecting the light incident from the incident surface in a direction different from the incident surface, and an emission surface for causing the light incident from a direction orthogonal to the incident surface and reflected from the reflecting surface to travel in a straight line, and emitting the light to the outside, an imaging device including a light receiving unit, formed on a surface of the imaging device, for receiving the light emitted from the emission surface and performing photoelectric conversion on the light, and a cylindrical imaging holder, protruding from at least part of an outer edge of one end in line with a side surface shape of the optical member, for defining the position of the incident surface and holding the optical member; and a lens unit including a lens for condensing light incident from one end and emitting the condensed light, and a hollow lens holder, including openings at both ends, for holding the lens.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
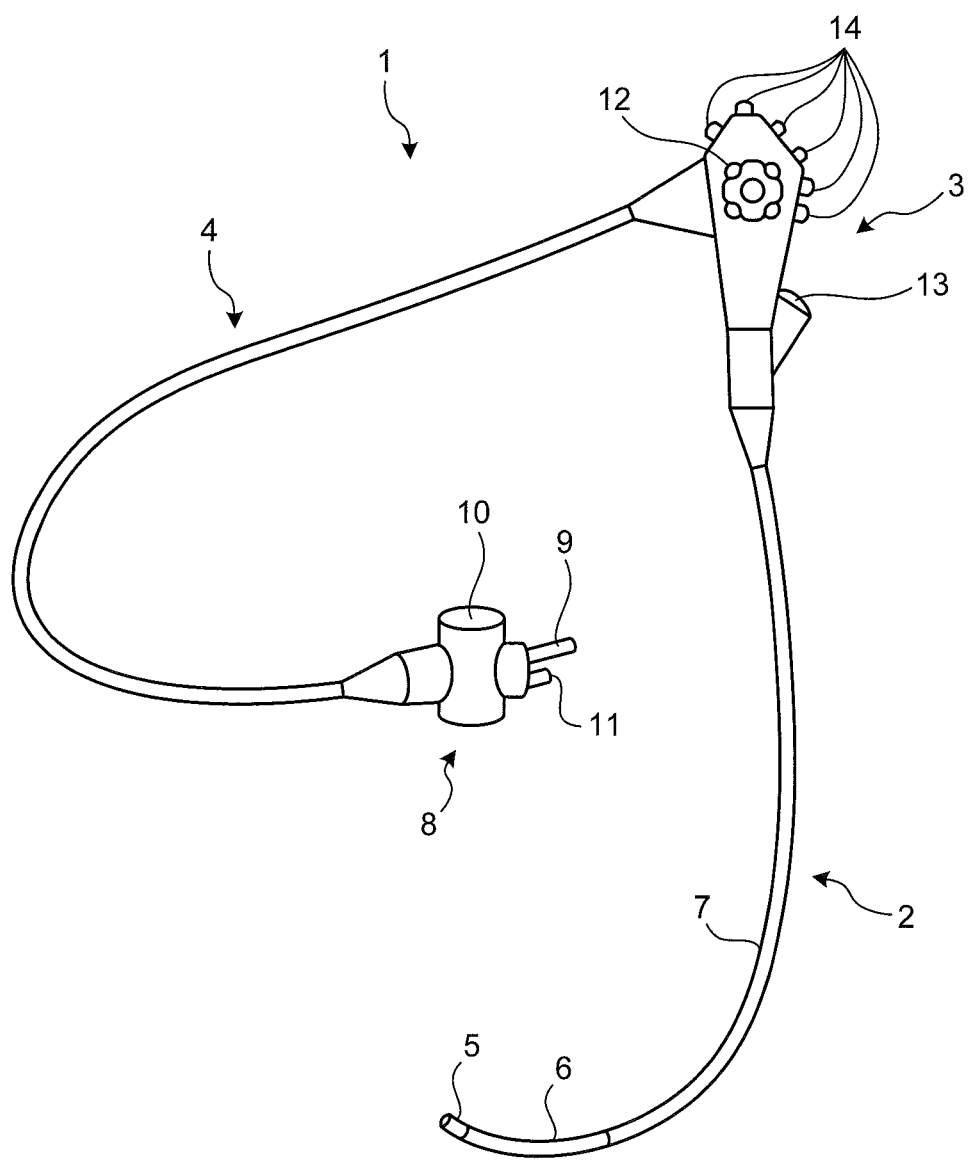
FIG. 1 is a schematic diagram illustrating an entire configuration of an endoscope apparatus according to a first embodiment of the present invention.

Hereinafter, embodiments of the present invention are described in detail with reference to the drawings. The present invention is not limited by the following embodiments. Moreover, the drawings referred to in the following description only schematically illustrate shapes, sizes, and positional relationships to such an extent that allows the understanding of the content of the present invention. In other words, the present invention is not limited only to the shapes, sizes, and positional relationships illustrated in the drawings.

First Embodiment

Firstly, an endoscope apparatus in a first embodiment is described. FIG. 1 is a diagram illustrating a schematic configuration of the endoscope apparatus in the first embodiment. As illustrated in FIG. 1, an endoscope apparatus 1 in the first embodiment includes a slim and long insertion section 2, an operation unit 3 on a proximal end side of the insertion section 2 for allowing an endoscope apparatus operator to grip, and a flexible universal cord 4 stretching from a side of the operation unit 3. A light guide cable, an electric system cable, and the like are, built in the universal cord 4.

The insertion section 2 includes a distal end section 5 with a built-in imaging module having an imaging device such as a CCD, a freely bendable bending section 6 including a plurality of bending pieces, and an extra long flexible tube section 7 provided on a proximal end side of the bending section 6, the flexible tube section 7 having flexibility.

A connector section 8 is provided at a stretching side end of the universal cord 4. The connector section 8 is provided with a light guide connector 9 connected detachably to a light source device, an electric contact section 10 for transmitting, to a signal processing device and a control device, an electric signal of an object image photoelectric converted by a CCD or the like, an air supply base 11 for supplying air to a nozzle of the distal end section 5, and the like. A halogen lamp or the like is built in the light source device, and light from the halogen lamp is supplied as illumination light to the endoscope apparatus 1 connected via the light guide connector 9. Moreover, the signal processing device and the control device are devices that supply power to the imaging device, into which a photoelectric converted electric signal is input from the imaging device. The devices process an electric signal imaged by the imaging device to display an image on a display device connected while controlling the gain adjustment and the like of the imaging device, and outputting a drive signal to drive the imaging device.

The operation unit 3 is provided with a bending knob 12 for bending the bending section 6 in the up and down direction and the right and left direction, a treatment instrument insertion section 13 for inserting a treatment instrument such as a biopsy forceps or a laser probe into the body cavity, and a plurality of switches 14 for performing operations of the signal processing device and the control device, or peripheral devices such as air supply, water supply, and gas supply means. The endoscope apparatus 1 with a treatment instrument inserted into a treatment instrument insertion port protrudes a distal end treatment section of the treatment instrument via a treatment instrument insertion channel provided on the inside and performs things such as biopsy to collect the tissue of an affected area by, for example, a biopsy forceps.

Figure 2:
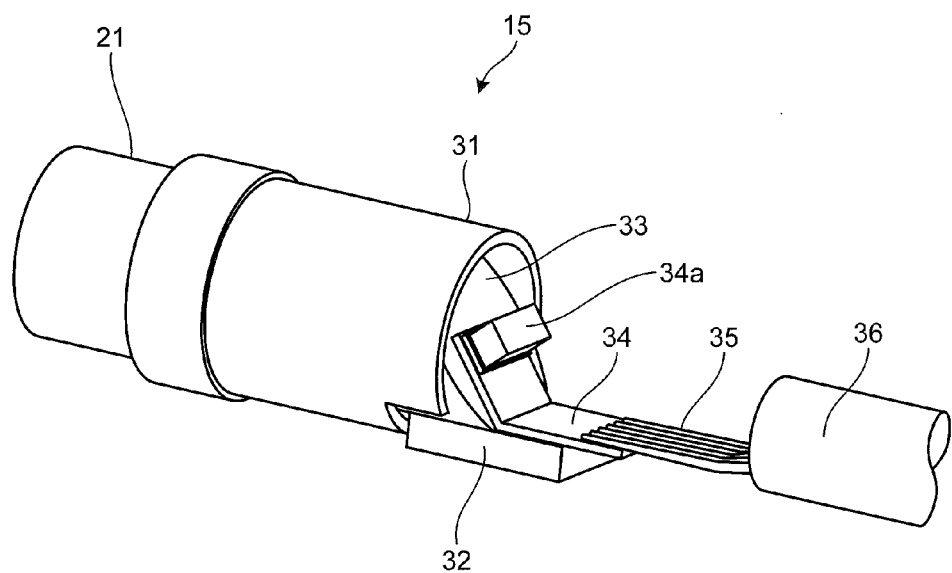
FIG. 2 is a perspective view illustrating an imaging module to be mounted on a distal end section of the endoscope apparatus illustrated in FIG. 1.
Figure 3:
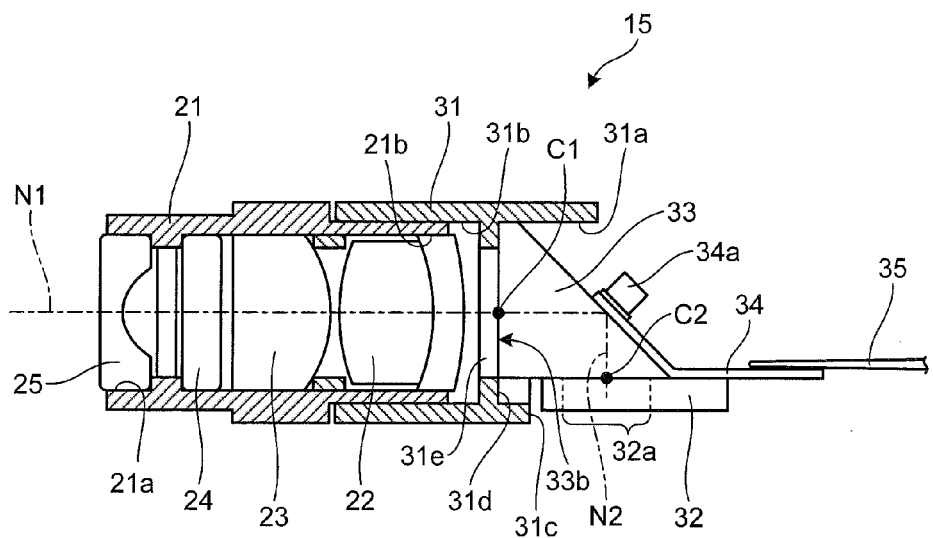
FIG. 3 is a partial sectional view illustrating the imaging module to be mounted on the distal end section of the endoscope apparatus illustrated in FIG. 1.
Figure 4:
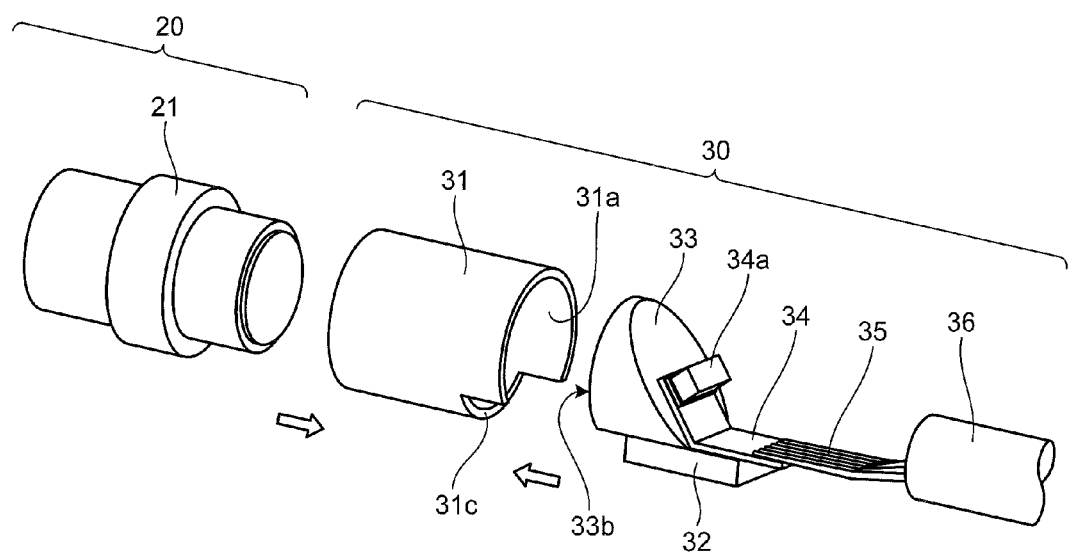
FIG. 4 is an exploded perspective view illustrating the imaging module to be mounted on the distal end section of the endoscope apparatus illustrated in FIG. 1.

Next, a description is given of the configuration of an imaging module mounted on the distal end section 5 of the endoscope apparatus 1. FIG. 2 is a perspective view illustrating the imaging module to be mounted on the distal end section of the endoscope apparatus illustrated in FIG. 1. FIG. 3 is a partial sectional view illustrating the imaging module to be mounted on the distal end section of the endoscope apparatus illustrated in FIG. 1. FIG. 4 is an exploded perspective view illustrating the imaging module to be mounted on the distal end section of the endoscope apparatus illustrated in FIG. 1. FIG. 3 is a cross-sectional view of an imaging unit illustrated in FIG. 2, and is a cross-sectional view when cut on a vertical plane with respect to a light receiving unit surface of the imaging device included in the imaging unit.

An imaging module 15 to be mounted on the distal end section 5 of the endoscope apparatus 1 illustrated in FIG. 1 includes a lens unit 20 having a plurality of objective lens and an imaging unit 30 having an imaging device 32 (see FIG. 4).

The lens unit 20 includes a hollow cylindrical lens holder 21 that comprises light-shielding material and has openings at both ends, lenses 22, 23 and 24 for condensing light from the outside, and an observation window 25 for transmitting the light from the outside.

The size of the opening of the lens holder 21 agrees with the outer peripheries of the lenses 22, 23 and 24 and the observation window 25. As illustrated in FIG. 3, the lenses 22, 23 and 24 and the observation window 25 are assembled inside the lens holder 21 such that their centers are respectively located on the same axis (an axis N1). Upon assembly of the optical members of the lens holder 21, the shapes of the optical members and the lens holder 21 are designed such that the center axis of the outer diameter of the lens holder 21 agrees with the centers of the lenses 22, 23 and 24, and the observation window 25, in other words, the optical axis center of the lens unit 20 including the lenses 22, 23 and 24, and the observation window 25. The lens holder 21 comprises, for example, corrosion-resistant steel, and at least its outside is shielded from light.

Light from the outside that has entered the inside of the lens holder 21 from an opening 21a at one end of the lens holder 21 via the observation window 25 is condensed by the lenses 22, 23 and 24. The condensed light condensed by the lenses 22, 23 and 24 is then emitted from an opening 21b at the other end of the lens holder 21. The thickness of the emission side end on the opening 21b side of the lens holder 21 is substantially uniform in any circumferential direction.

The imaging unit 30 includes a hollow imaging holder 31 having openings at both ends, an imaging device 32 that receives light from an imaging target and performs photoelectric conversion on the light, a prism 33 mounted on the imaging device 32, and a base plate 34, mounted on the imaging device 32 and the prism 33, for being electrically connected to the imaging device 32. The imaging holder 31 comprises, for example, corrosion-resistant steel.

The imaging device 32 is a bare chip semiconductor device illustrated as a CCD, CMOS image sensor, or the like, and has an imaging function that receives light from an object and images the object's image. As illustrated in FIG. 3, in the imaging device 32, a light receiving unit 32a that receives light from an object and performs a photoelectric conversion process on the received light is formed on a top surface of a chip substrate. The imaging device 32 is placed such that the optical axis of the lens unit 20 is substantially parallel to the surface of the light receiving unit 32a when the imaging unit 30 is in finished form.

The light receiving unit 32a is realized using a group of pixels arranged in a predetermined form such as a lattice form, a microlens formed on the group of pixels to condense light efficiently, and the like. The surface of the light receiving unit 32a forms a rectangle. The light receiving unit 32a is formed at a predetermined position on the chip substrate of the imaging device 32. Moreover, the imaging device 32 includes a drive circuit unit (not illustrated) where a drive circuit for executing an imaging operation is formed, and an external connection electrode (not illustrated).

The external connection electrode of the imaging device 32 is connected by a conductor wire 35 to an external connection electrode of the base plate 34. At this point in time, in the imaging device 32, the base plate 34 is mounted on a surface where the light receiving unit 32a has been formed. The light receiving unit 32a performs the photoelectric conversion process on the received light. The drive circuit unit generates an image signal of the object based on the signal on which the photoelectric conversion process has been performed in the light receiving unit 32a, and outputs the generated image signal to the base plate 34 via the external connection electrode. With respect to the image signal that has been output to the base plate 34, the image signal is transmitted by a wiring cable 36 to the signal processing device and the control device via the conductor wire 35 connected to the base plate 34. A signal control component 34a may be implemented on the base plate 34.

Figure 5:
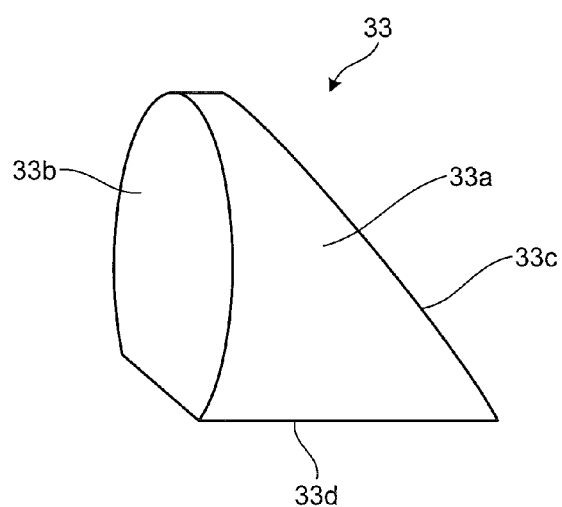
FIG. 5 is a perspective view illustrating a prism of the imaging module illustrated in FIG. 2.
Figure 6:
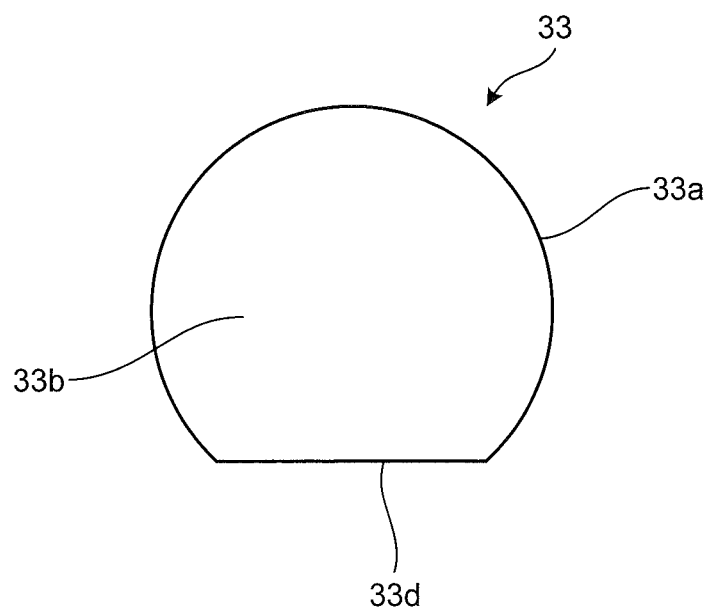
FIG. 6 is a side view illustrating the prism of the imaging module illustrated in FIG. 2.

FIG. 5 is a perspective view illustrating the prism 33 of the imaging module 15 illustrated in FIG. 2. FIG. 6 is a side view illustrating the prism of the imaging module illustrated in FIG. 2. The prism 33 is mounted on the light receiving unit 32a of the imaging device 32 and refracts the light from the outside. The prism 33 is formed using a columnar member as illustrated in FIGS. 5 and 6, and includes: a side surface portion 33a forming a side surface where a cross section perpendicular to the center axis of the column forms a substantially arc shape; an incident surface 33b that is provided at one end of the side surface portion 33a, has a flat surface orthogonal to the center axis of the column, and allows the light from the lens holder 21 to enter; a reflecting surface 33c that is provided at the other end of the side surface portion 33a, has a flat surface inclined with respect to the center axis of the column, and reflects the light incident on the incident surface 33b; and an emission surface 33d that is on a side where the distance between the incident surface 33b and the reflecting surface 33c extends, is provided on a side surface through which the optical axis of the light incident from a direction orthogonal to the incident surface 33b and reflected from the reflecting surface 33c passes, extends in a planar form in the cylinder's center axis direction, and causes the light reflected from the reflecting surface 33c to travel in a straight line and be emitted to the outside. The side surface portion 33a (the incident surface 33b) has a substantially circular shape when viewed from a light incident direction (a direction with the incident surface 33b as the front).

The light refracted by the prism 33 toward an axis N2 direction is emitted from the emission surface 33d and received by the light receiving unit 32a of the imaging device 32. Moreover, a recess (not illustrated) for forming an air gap directly above the microlens of the light receiving unit 32a is formed in the bottom surface (the emission surface 33d) of the prism 33. Moreover, as illustrated in FIG. 3, the prism 33 is implemented on the imaging device 32 such that the light that has passed a position indicated by a point C1 of the incident surface 33b of the prism 33 reaches a center C2 of the light receiving unit 32a of the imaging device 32 after being refracted by the refracting surface of the prism 33. The point C1 corresponds to the center of a reference area being an area where the light received by the light receiving unit 32a enters, within the incident surface 33b of the prism 33.

Figure 7:
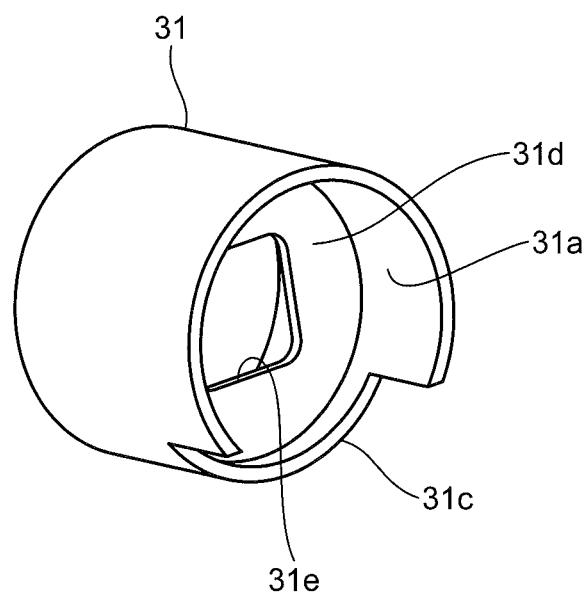
FIG. 7 is a perspective view illustrating an imaging holder of the imaging module illustrated in FIG. 2.

FIG. 7 is a perspective view illustrating the imaging holder 31 of the imaging module 15 illustrated in FIG. 2. The imaging holder 31 has a substantially cylindrical shape and is for housing parts of the lens holder 21 and the prism 33 therein. The imaging holder 31 includes a prism side opening 31a that is provided at one end and forms a cylindrical internal space in line with the diameter (maximum diameter) of the incident surface 33b of the prism 33, a lens side opening 31b (see FIG. 3) that is provided at the other end and forms an internal space in line with the diameter of the outer periphery of a connection side end of the lens holder 21, and a flat plate portion 31d that is provided at the end on the inner side of the prism side opening 31a and has a flat plate shape orthogonal to the center axis of the cylinder. Moreover, the prism side opening 31a includes a cutout portion 31c having a cut shape where part of the side surface of the cylinder is cut out. A hole 31e for allowing the light from the lens holder 21 to pass through is formed in the flat plate portion 31d.

The imaging holder 31 houses the prism 33 on which the imaging device 32 and the base plate 34 are implemented in the prism side opening 31a, and the prism 33 is assembled in the imaging holder 31 while the lens holder 21 is assembled in the lens side opening 31b in the imaging holder 31. Upon assembly, the incident surface 33b of the prism 33 is brought into contact with the flat plate portion 31d of the imaging holder 31 and is in surface contact. At this point in time, a flare diaphragm may be inserted between the incident surface 33b of the prism 33 and the flat plate portion 31d of the imaging holder 31. Alternatively, a flare diaphragm may be evaporatively deposited on the incident surface 33b of the prism 33 (not illustrated). Consequently, the positions of the imaging holder 31 and the prism 33 with respect to the axis N1 direction are determined.

Figure 8:
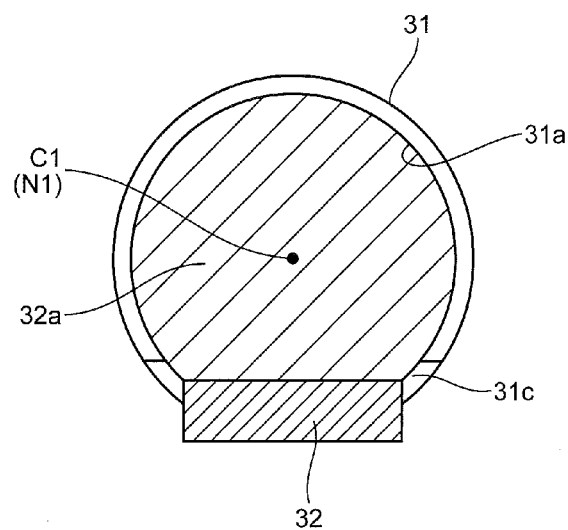
FIG. 8 is a partial sectional view illustrating the imaging module illustrated in FIG. 2.

At this point in time, as illustrated in FIG. 8, part of the outer peripheral surface of the incident surface 33b of the prism 33 is fixed in contact with the inner peripheral surface of the prism side opening 31a of the imaging holder 31. The inner peripheral surface of the prism side opening 31a is in contact along the outer periphery of the prism 33. Accordingly, the prism side opening 31a holds the prism 33 such that the point C1 is located on the axis N1 even if the prism 33 rotates along the inner peripheral surface. In other words, the prism side opening 31a prevents the deviation of the optical axis of the prism 33 by holding the prism 33 with its inner peripheral surface.

It is set here such that the outer diameter of the light emission side end of the lens holder 21 agrees with the inner diameter of the light incident side end of the imaging holder 31. In other words, the outer diameter of the opening on the imaging holder 31 connection side of the lens holder 21 has the same diameter as the inner diameter of the lens side opening 31b of the imaging holder 31.

Hence, the light emission side end of the lens holder 21 can be fitted directly into the light incident side end of the imaging holder 31 by inserting the light emission side end of the lens holder 21 into the imaging holder 31 as indicated by the arrows illustrated in FIG. 4.

In this manner, the shapes of the lens holder 21 and the imaging holder 31 are designed based on the sizes of the components of the lens unit 20, the sizes of the components of the imaging holder 31, and the optical axis of the optical systems such that the optical axis center of the lenses 22, 23 and 24 assembled to the lens holder 21 pass the point C1 that is the center of the reference area of the prism 33 fixed on the inside of the imaging holder 31 upon the fitting of the light emission side end of the lens holder 21 and the light incident side end of the imaging holder 31. Moreover, part of the side surface portion 33a of the prism 33 is held along the inner peripheral surface of the prism side opening 31a of the imaging holder 31. Accordingly, the position is defined by the inner peripheral surface of the prism side opening 31a of the imaging holder 31 such that the optical axis center of the lens unit 20 and the point C1 being the center of the reference area of the incident surface 33b of the prism 33 are located on the same axis N1.

Moreover, the prism 33 is implemented on the imaging device 32 such that the light passing the point C1 being the center of the reference area of the incident surface 33b of the prism 33 reaches the center C2 of the light receiving unit 32a. Hence, the condensed light by the lenses 22, 23 and 24 of the lens holder 21 is incident on the incident surface 33b of the prism 33 in a state where the optical axis center agrees with the center of the light receiving unit 32a of the imaging device 32. Therefore, the optical axis center of the optical members including the lenses 22, 23 and 24 of the lens unit 20 agrees with the center of the light received by the light receiving unit 32a of the imaging device 32 of the imaging unit 30 upon the fitting of the light emission side end of the lens holder 21 and the light incident side end of the imaging holder 31.

According to the above-mentioned first embodiment, the positions of the condensed light emission side end of the lens holder 21 and the outer periphery of the prism 33 are defined by the inner peripheral surface of the imaging holder 31 such that the optical axis center passing the centers of the lenses 22, 23 and 24 agrees with the point C1 being the center of the incident surface 33b of the prism 33 in the imaging module 15. Hence, in a simple manufacturing process of simply fitting the condensed light emission side end of the lens holder 21, and the end on the incident surface 33b side of the prism 33 respectively into the openings at both ends of the imaging holder 31, it is possible to manufacture the imaging module where the optical axis center of the optical members of the lens unit 20 is caused to agree with the center of the light received by the light receiving unit 32a of the imaging device 32 of the imaging unit 30.

The outer peripheral shape of the prism side opening 31a of the imaging holder 31 has an arc shape in line with the outer periphery on the incident surface 33b side of the prism 33. Accordingly, the prism 33 can be fitted into the imaging holder 31 regardless of the relative position in the circumferential direction. Hence, fitting can be performed more easily than a case where the outer peripheral shape of the prism 33 is a square.

Moreover, in the imaging module 15, the condensed light emission side end of the lens holder 21, and the incident surface 33b side end of the prism 33 can be fitted directly into both ends of the imaging holder 31 without another intervening member. Accordingly, it is possible to promote the downsizing of the diameter of the distal end section of the insertion tool of the endoscope apparatus, and it is also possible to reduce the amount of light lost due to an intervening member and acquire a fine image.

Second Embodiment

Next, a second embodiment is described. In the second embodiment, an imaging module assembled by inserting a lens holder into an imaging holder is described. The same reference numerals are assigned to the same elements as those described above in FIG. 2 and the like.

Figure 9:
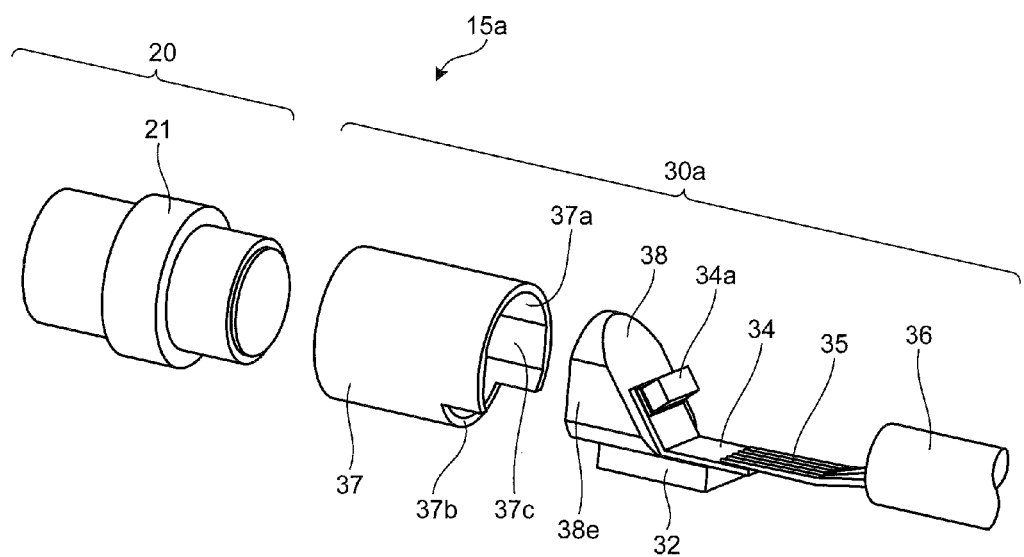
FIG. 9 is an exploded perspective view illustrating an imaging module according to a second embodiment of the present invention.

FIG. 9 is an exploded perspective view illustrating an imaging module 15a according to the second embodiment. As illustrated in FIG. 9, the imaging module 15a according to the second embodiment includes the above-mentioned lens unit 20, and an imaging unit 30a having the imaging device 32.

The imaging unit 30a includes a hollow imaging holder 37 having openings at both ends, the imaging device 32 that performs photoelectric conversion on light from an imaging target, and a prism 38 mounted on the imaging device 32. The imaging holder 37 comprises, for example, corrosion-resistant steel.

Figure 10:
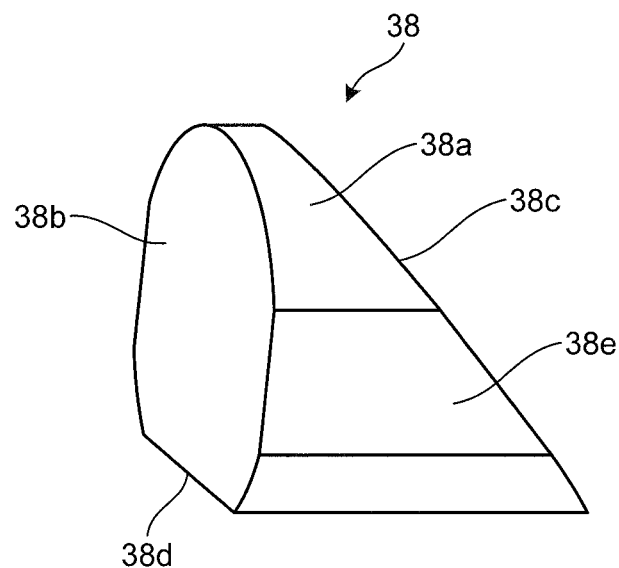
FIG. 10 is a perspective view illustrating a prism of the imaging module illustrated in FIG. 9.
Figure 11:
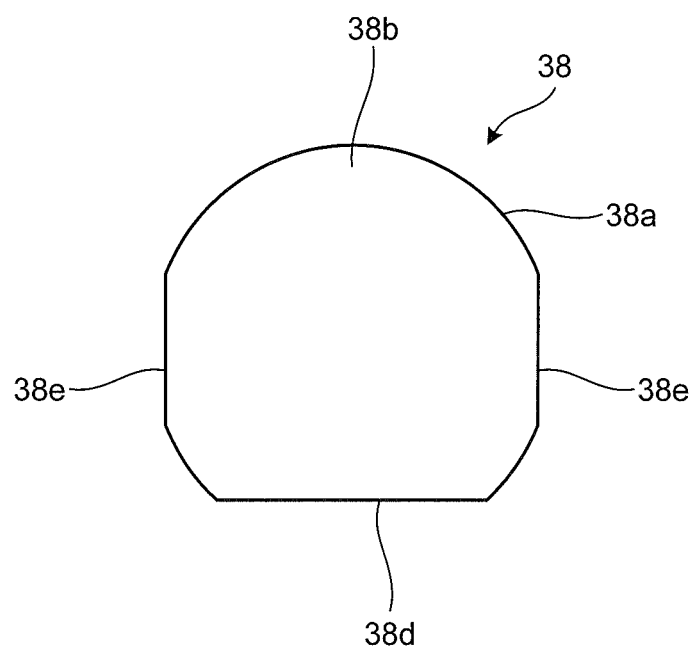
FIG. 11 is a side view illustrating the prism of the imaging module illustrated in FIG. 9.

FIG. 10 is a perspective view illustrating the prism 38 of the imaging module 15a illustrated in FIG. 9. FIG. 11 is a side view illustrating the prism 38 of the imaging module 15a illustrated in FIG. 9. The prism 38 is mounted on the light receiving unit 32a (see FIG. 3) of the imaging device 32 and refracts light from the outside. The prism 38 is formed using a columnar member as illustrated in FIGS. 10 and 11, and includes a side surface portion 38a forming a side surface where a cross section perpendicular to the center axis of the column has a substantially arc shape, an incident surface 38b that is provided at one end of the side surface portion 38a, has a flat surface orthogonal to the center axis of the cylinder, and allows the light from the lens holder 21 to enter, a reflecting surface 38c that is provided at the other end of the side surface portion 38a, has a flat surface inclined with respect to the center axis of the cylinder, and reflects the light incident on the incident surface 38b, and an emission surface 38d that is on a side where the distance between the incident surface 38b and the reflecting surface 38c extends, is provided on a side surface through which the optical axis of the light incident from a direction orthogonal to the incident surface 38b and reflected from the reflecting surface 38c passes, extends in a planar form in the cylinder's center axis direction, and causes the light reflected from the reflecting surface 38c to travel in a straight line and be emitted to the outside. The side surface portion 38a (the incident surface 38b) has a substantially circular shape when viewed from a light incident direction (a direction with the incident surface 38b as the front).

Moreover, the prism 38 includes a plurality of (two in the second embodiment) prism side flat surface portions 38e that is provided in locations on the side surface portion 38a, the locations being different from the emission surface 38d, and extends in a planar form in the center axis direction of the cylinder. It is preferred that the prism side flat surface portions 38e be provided on the outer peripheral side located on the diameter (maximum diameter) of the side surface portion 38a.

Figure 12:
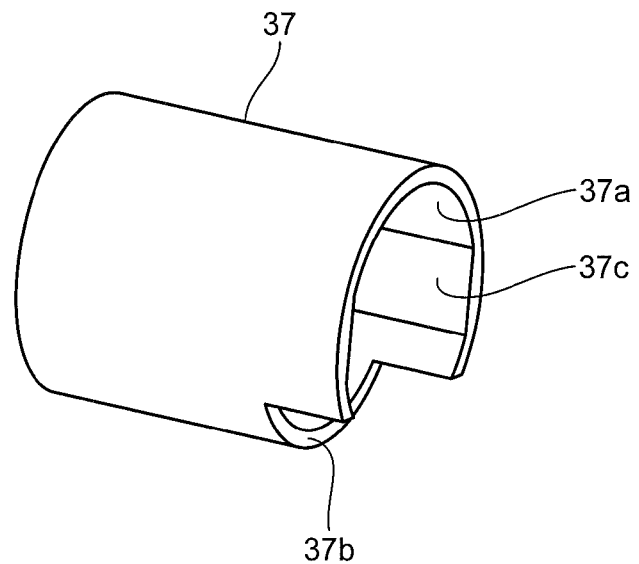
FIG. 12 is a perspective view illustrating an imaging holder of the imaging module illustrated in FIG. 9.

FIG. 12 is a perspective view illustrating the imaging holder 37 of the imaging module 15a illustrated in FIG. 9. The imaging holder 37 includes a similar configuration to the above-mentioned imaging holder 31, and includes a prism side opening 37a forming a cylindrical internal space in line with the diameter (maximum diameter) of the incident surface 38b of the prism 38, instead of the prism side opening 31a. Moreover, the prism side opening 37a includes a cutout portion 37b having a cut shape where part of the side surface of the cylinder is cut out, and a plurality of (two in the second embodiment) holder side flat surface portions 37c provided on the inner peripheral surface of the prism side opening 37a in line with the relative positional relationships with the prism side flat surface portions 38e.

Figure 13:
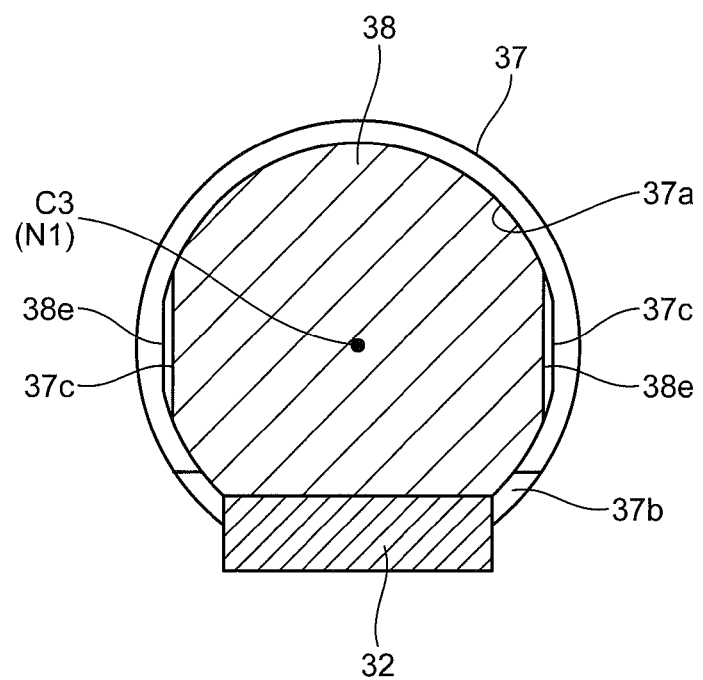
FIG. 13 is a partial sectional view illustrating the imaging module illustrated in FIG. 9.

The imaging holder 37 houses the prism 38 on which the imaging device 32 and the base plate 34 are implemented, in the prism side opening 37a, and the prism 38 is assembled in the imaging holder 37. At this point in time, as illustrated in FIG. 13, part of the side surface portion 38a of the prism 38 is fixed in contact with an inner peripheral surface of the prism side opening 37a of the imaging holder 37. The inner peripheral surface of the prism side opening 37a is in contact along the outer periphery of the prism 38. Accordingly, the prism side opening 37a holds the prism 38 such that a point C3 is located on the axis N1 even if the prism 38 rotates along the inner peripheral surface. In other words, the prism side opening 37a prevents the deviation of the optical axis of the prism 38 by holding the prism 38 with its inner peripheral surface. The distance between the holder side flat surface portions 37c is designed to be longer than the distance between the prism side flat surface portions 38e.

Part of the outer peripheral surface of the incident surface 38b of the prism 33 is held along the inner peripheral surface of the prism side opening 37a of the imaging holder 37. Accordingly, the position is defined by the inner peripheral surface of the prism side opening 37a of the imaging holder 37 such that the optical axis center of the lens unit 20 and the point C3 being the center of the reference area of the incident surface 38b of the prism 38 are located on the same axis N1. Moreover, when the prism 38 rotates about the center axis in a state of being fitted into the imaging holder 37, ends of the prism side flat surface portions 38e come into contact with the holder side flat surface portions 37c. Accordingly, the amount of rotation of the prism 38 in the prism side opening 37a is regulated.

Moreover, as in the above-mentioned first embodiment, the prism 38 is implemented on the imaging device 32 such that the light passing the point C3 being the center of the reference area of the incident surface 38b of the prism 38 reaches the center C2 (see FIG. 3) of the light receiving unit 32a. Hence, the condensed light by the lenses 22, 23 and 24 of the lens holder 21 is incident on the incident surface 38b of the prism 38 in a state where the optical axis center agrees with the center of the light receiving unit 32a of the imaging device 32. Therefore, the optical axis center of the optical members including the lenses 22, 23 and 24 of the lens unit 20 agrees with the center of the light received by the light receiving unit 32a of the imaging device 32 of the imaging unit 30a upon the fitting of the light emission side end of the lens holder 21 and the light incident side end of the imaging holder 37.

According to the above-mentioned second embodiment, as in the first embodiment, the positions of the condensed light emission side end of the lens holder 21 and the outer periphery of the prism 38 are defined by the inner peripheral surface of the imaging holder 37 such that the optical axis center passing the centers of the lenses 22, 23 and 24 agrees with the point C3 being the center of the incident surface 33b of the prism 33 in the imaging module 15a. Hence, in a simple manufacturing process of simply fitting the condensed light emission side end of the lens holder 21, and the end on the incident surface 38b side of the prism 38 respectively into the openings at both ends of the imaging holder 37, it is possible to manufacture the imaging module where the optical axis center of the optical members of the lens unit 20 is caused to agree with the center of the light received by the light receiving unit 32a of the imaging device 32 of the imaging unit 30a.

The outer peripheral shape of the prism side opening 37a of the imaging holder 37 has an arc shape in line with the outer periphery on the incident surface 38b side of the prism 38. Accordingly, the prism 38 can be fitted into the imaging holder 37 regardless of the relative positions in the circumferential direction. Hence, fitting can be performed more easily than a case where the outer peripheral shape of the prism 38 is a square.

Moreover, the amount of rotation of the prism 38 in the imaging holder 37 can be regulated by the holder side flat surface portions 37c of the imaging holder 37 and the prism side flat surface portions 38e of the prism 38. Accordingly, it is possible to achieve facilitation of fitting and roughly determine the position of the prism 38 with respect to the imaging holder 37 in the circumferential direction.

Third Embodiment

Next, a third embodiment is described. In the third embodiment, an imaging module assembled by inserting a lens holder into an imaging holder is described. The same reference numerals are assigned to the same elements as those described above in FIG. 2 and the like.

Figure 14:
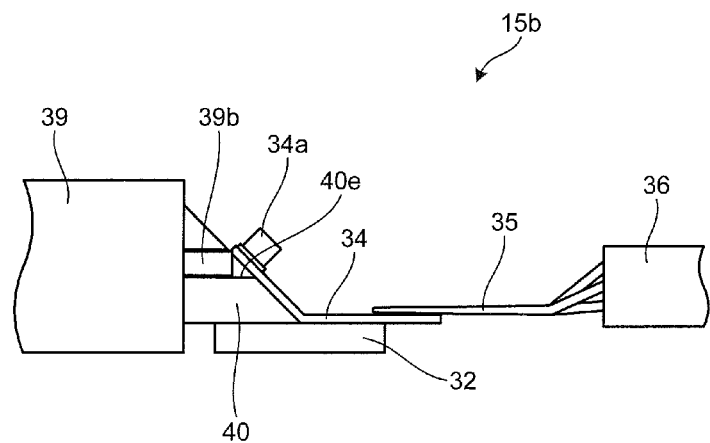
FIG. 14 is a side view illustrating an imaging module according to a third embodiment of the present invention.
Figure 15:
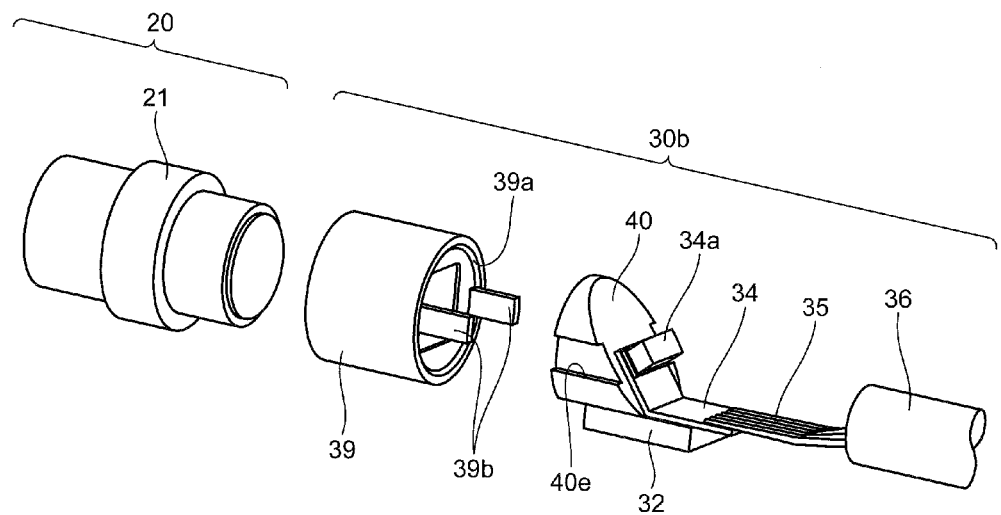
FIG. 15 is an exploded perspective view illustrating the imaging module according to the third embodiment of the present invention.

FIG. 14 is a side view illustrating an imaging module 15b according to the third embodiment. FIG. 15 is an exploded perspective view illustrating the imaging module 15b according to the third embodiment. As illustrated in FIGS. 14 and 15, the imaging module 15b according to the third embodiment includes the above-mentioned lens unit 20, and an imaging unit 30b having the imaging device 32.

The imaging unit 30b includes a hollow imaging holder 39 having openings at both ends, the imaging device 32 that performs photoelectric conversion on light from an imaging target, and a prism 40 mounted on the imaging device 32. The imaging holder 39 comprises, for example, corrosion-resistant steel.

Figure 16:
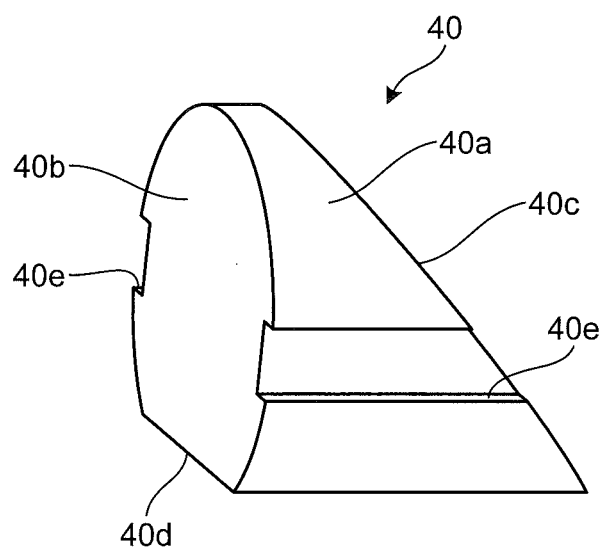
FIG. 16 is a perspective view illustrating a prism of the imaging module illustrated in FIG. 14.
Figure 17:
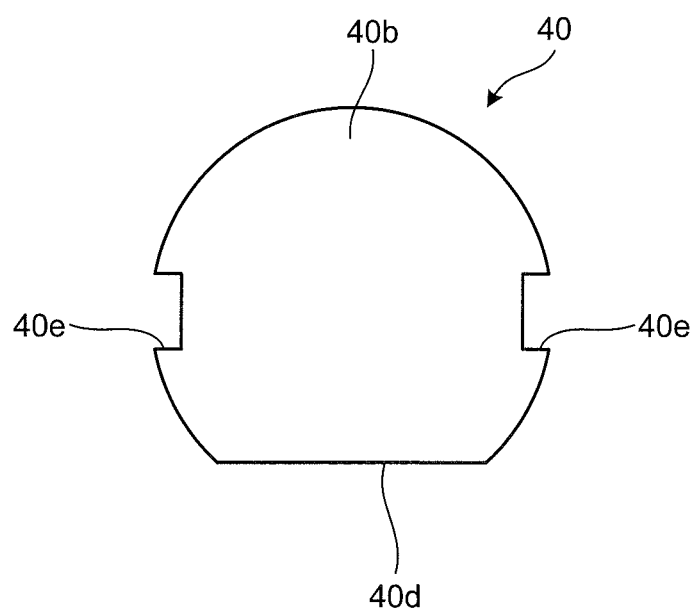
FIG. 17 is a side view illustrating the prism of the imaging module illustrated in FIG. 14.

FIG. 16 is a perspective view illustrating the prism 40 of the imaging module 15b illustrated in FIG. 14. FIG. 17 is a side view illustrating the prism 40 of the imaging module 15b illustrated in FIG. 14. The prism 40 is mounted on the light receiving unit 32a (see FIG. 3) of the imaging device 32 and refracts light from the outside. As illustrated in FIGS.

16 and 17, the prism 40 includes a side surface portion 40a forming a side surface where a cross section has a substantially circular shape, an incident surface 40b that is provided at one end of the side surface portion 40a, has a flat surface orthogonal to the center axis of the cylinder, and allows the light from the lens holder 21 to enter, a reflecting surface 40c that is provided at the other end of the side surface portion 40a, has a flat surface inclined with respect to the center axis of the cylinder, and reflects the light incident on the incident surface 40b, and an emission surface 40d that is on a side where the distance between the incident surface 40b and the reflecting surface 40c extends, is provided on a side surface through which the optical axis of the light incident from a direction orthogonal to the incident surface 40b and reflected from the reflecting surface 40c passes, extends in a planar form in the cylinder's center axis direction, and causes the light reflected from the reflecting surface 40c to travel in a straight line and be emitted to the outside.

Moreover, the prism 40 includes a plurality of (two in the third embodiment) recesses 40e that is provided in locations on the side surface portion 40a, the locations being different from the emission surface 40d, extends in the center axis direction of the cylinder, and has a concave shape that opens toward the outside. It is preferred that the recesses 40e be provided on the outer peripheral side located on the diameter (maximum diameter) of the side surface portion 40a.

Figure 18:
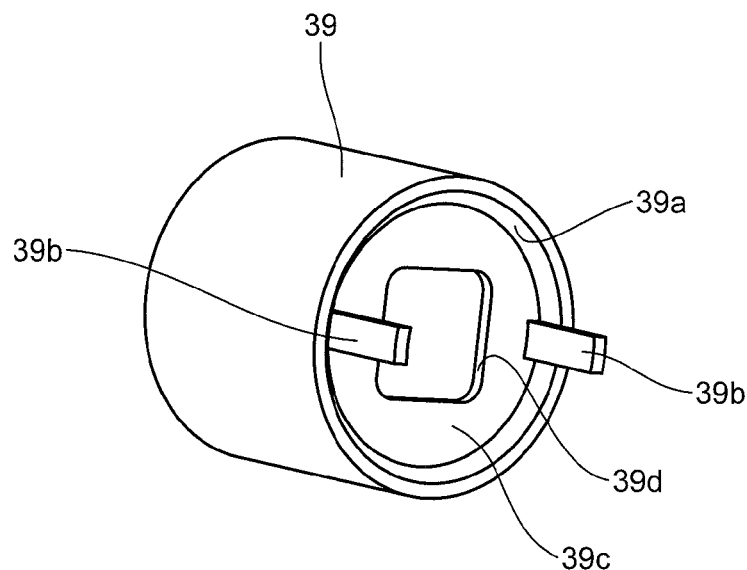
FIG. 18 is a perspective view illustrating an imaging holder of the imaging module illustrated in FIG. 14.

FIG. 18 is a perspective view illustrating the imaging holder 39 of the imaging module 15b illustrated in FIG. 14. The imaging holder 39 includes a similar configuration to the above-mentioned imaging holder 31, on a side coupled to the lens unit 20, and includes a prism side opening 39a that is provided at an end on a different side from the side coupled to the lens unit 20, and forms a cylindrical internal space in line with the diameter (maximum diameter) of the incident surface 40b of the prism 40, and a flat plate portion 39c that is provided at the end on the inside of the prism side opening 39a and has a flat plate shape orthogonal to the center axis of the cylinder. Moreover, the prism side opening 39a includes a plurality of (two in the third embodiment) protrusions 39b that is provided on the inner peripheral surface of the prism side opening 39a in line with the relative positional relationships with the recesses 40e, and protrudes in a flat plate form from the flat plate portion 39c along the inner wall surface of the prism side opening 39a. A hole 39d for allowing the light from the lens holder 21 to pass through is formed in the flat plate portion 39c.

Figure 19:
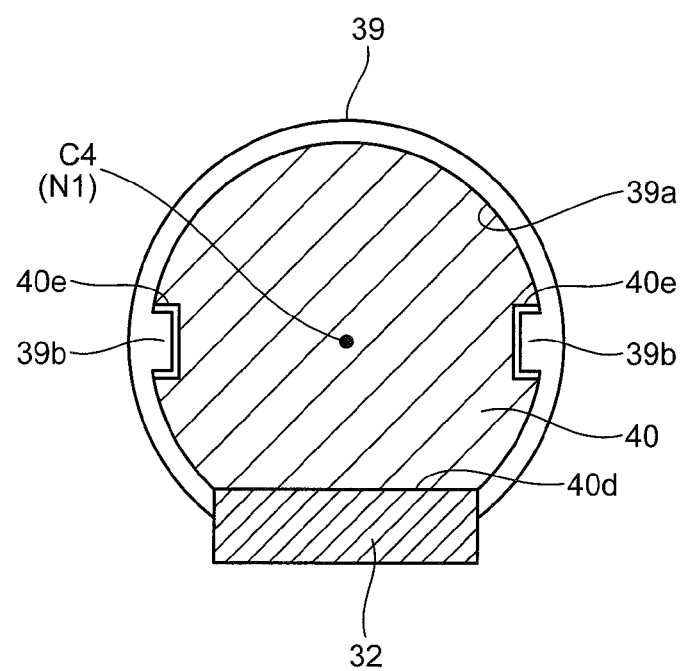
FIG. 19 is a partial sectional view illustrating the imaging module illustrated in FIG. 14.

The imaging holder 39 houses the prism 40 on which the imaging device 32 and the base plate 34 are implemented in the prism side opening 39a, and the prism 40 is assembled in the imaging holder 39. At this point in time, as illustrated in FIG. 19, part of the side surface portion 40a of the prism 40 is fixed in contact with the inner peripheral surface of the prism side opening 39a of the imaging holder 39. The inner peripheral surface of the prism side opening 39a is in contact along the outer periphery of the prism 40. Accordingly, the prism side opening 39a holds the prism 40 such that a point C4 is located on the axis N1 even if the prism 40 rotates along the inner peripheral surface. In other words, the prism side opening 39a prevents the deviation of the optical axis of the prism 40 by holding the prism 40 with its inner peripheral surface. The area of a region of the recess 40e where the protrusion 39b is housed is designed to be larger than the area of the protrusion 39b in a cross section in a direction orthogonal to the axis N1 (see FIG. 3).

Part of the outer peripheral surface of the incident surface 40b of the prism 40 is held along the inner peripheral surface of the prism side opening 39a of the imaging holder 39. Accordingly, the position is defined by the inner peripheral surface of the prism side opening 39a of the imaging holder 39 such that the optical axis center of the lens unit 20 and the point C4 being the center of the reference area of the incident surface 40b of the prism 40 are located on the same axis N1. Moreover, when the prism 40 rotates about the center axis in a state of being fitted into the imaging holder 39, the protrusion 39b comes into contact with the inner wall surface of the recess 40e. Accordingly, the amount of rotation of the prism 40 in the prism side opening 39a is regulated.

Moreover, as in the above-mentioned first embodiment, the prism 40 is implemented on the imaging device 32 such that the light passing the point C4 being the center of the reference area of the incident surface 40b of the prism 40 reaches the center C2 (see FIG. 3) of the light receiving unit 32a. Hence, the condensed light by the lenses 22, 23 and 24 of the lens holder 21 is incident on the incident surface 40b of the prism 40 in a state where the optical axis center agrees with the center of the light receiving unit 32a of the imaging device 32. Therefore, the optical axis center of the optical members including the lenses 22, 23 and 24 of the lens unit 20 agrees with the center of the light received by the light receiving unit 32a of the imaging device 32 of the imaging unit 30b upon the fitting of the light emission side end of the lens holder 21 and the light incident side end of the imaging holder 39.

According to the above-mentioned third embodiment, as in the first embodiment, the positions of the condensed light emission side end of the lens holder 21 and the outer periphery of the prism 40 are defined by the inner peripheral surface of the imaging holder 39 such that the optical axis center passing the centers of the lenses 22, 23 and 24 agrees with the point C4 being the center of the incident surface 40b of the prism 40 in the imaging module 15b. Hence, in a simple manufacturing process of simply fitting the condensed light emission side end of the lens holder 21, and the end on the incident surface 40b side of the prism 40 respectively into the openings at both ends of the imaging holder 39, it is possible to manufacture the imaging module where the optical axis center of the optical members of the lens unit 20 is caused to agree with the center of the light received by the light receiving unit 32a of the imaging device 32 of the imaging unit 30b.

The outer peripheral shape of the prism side opening 39a of the imaging holder 39 has an arc shape in line with the outer periphery on the incident surface 40b side of the prism 40. Accordingly, the prism 40 can be fitted into the imaging holder 39 regardless of the relative positions in the circumferential direction. Hence, fitting can be performed more easily than a case where the outer peripheral shape of the prism 40 is a square.

Moreover, the amount of rotation of the prism 40 in the imaging holder 39 can be regulated by the protrusions 39b of the imaging holder 39 and the recesses 40e of the prism 40. Accordingly, it is possible to achieve facilitation of fitting and roughly determine the position of the prism 40 with respect to the imaging holder 39 in the circumferential direction.

Fourth Embodiment

Next, a fourth embodiment is described. In the fourth embodiment, an imaging module assembled by inserting a lens holder into an imaging holder is described. The same reference numerals are assigned to the same elements as those described above in FIG. 2 and the like.

Figure 20:
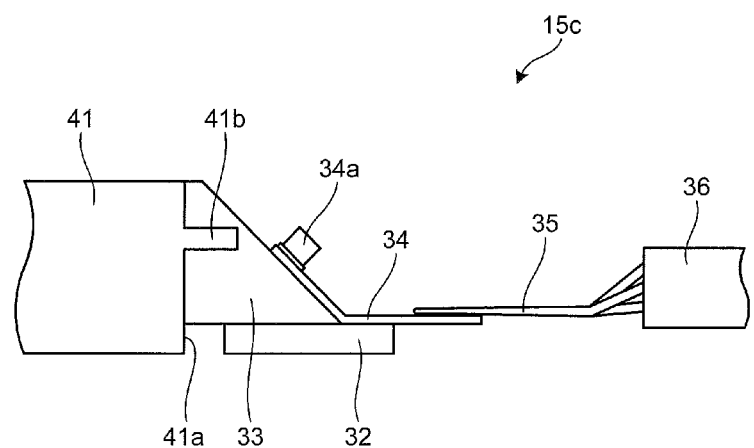
FIG. 20 is a side view illustrating an imaging module according to a fourth embodiment of the present invention.
Figure 21:
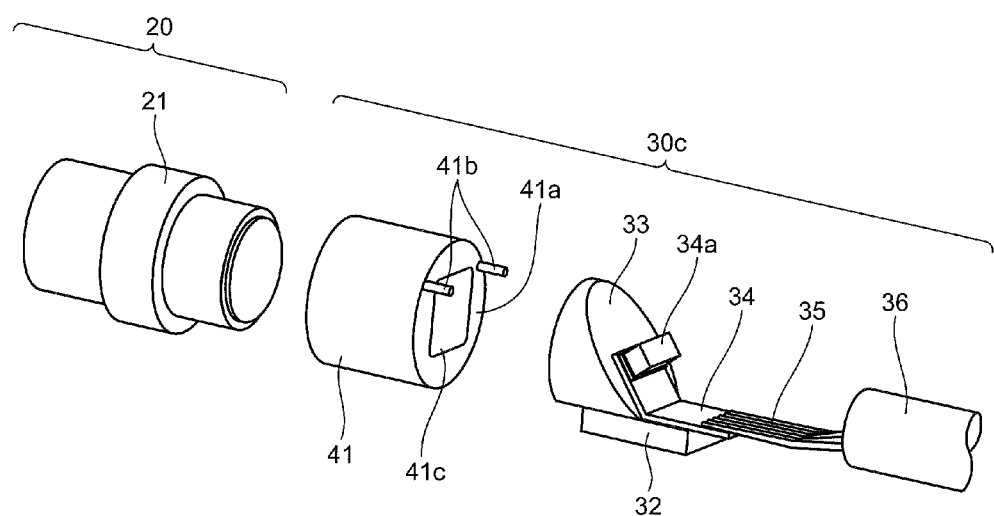
FIG. 21 is an exploded perspective view illustrating the imaging module according to the fourth embodiment of the present invention.

FIG. 20 is a side view illustrating an imaging module 15c according to the fourth embodiment. FIG. 21 is an exploded perspective view illustrating the imaging module 15c according to the fourth embodiment. As illustrated in FIGS. 20 and 21, the imaging module 15c according to the fourth embodiment includes the above-mentioned lens unit 20, and an imaging unit 30c having the imaging device 32.

The imaging unit 30c includes a hollow imaging holder 41 having openings at both ends, and the above-mentioned imaging device 32 and prism 33. The imaging holder 41 comprises, for example, corrosion-resistant steel.

Figure 22:
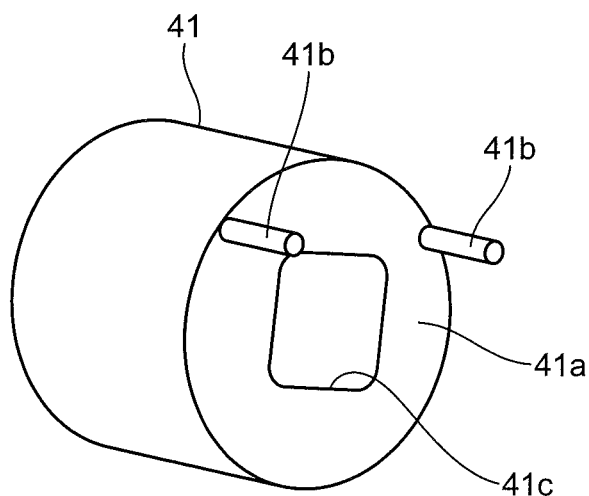
FIG. 22 is a perspective view illustrating an imaging holder of the imaging module illustrated in FIG. 20.

FIG. 22 is a perspective view illustrating the imaging holder 41 of the imaging module 15c illustrated in FIG. 20. The imaging holder 41 has a cylindrical shape having a diameter larger than the diameter (maximum diameter) of the incident surface 33b of the prism 33, has a similar configuration to the above-mentioned imaging holder 31, on a side coupled to the lens unit 20, and includes a flat plate portion 41a that is provided at an end on a different side from the side coupled to the lens unit 20, and has a flat plate shape orthogonal to the center axis of the cylinder. Moreover, the flat plate portion 41a includes a plurality of (two in the fourth embodiment) rodlike members 41b protruding in a rod shape from an outer edge toward the cylinder's center axis direction. Moreover, a hole 41c for allowing the light from the lens holder 21 to pass through is formed in the flat plate portion 41a.

Figure 23:
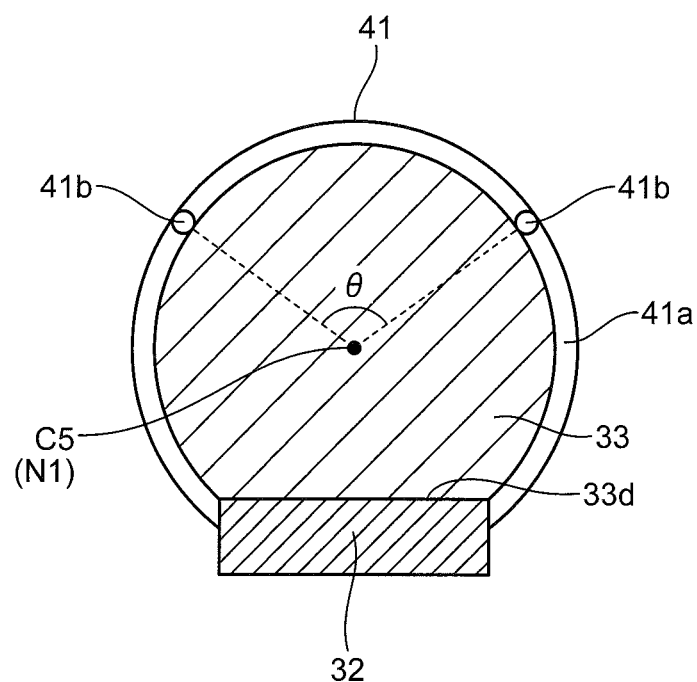
FIG. 23 is a partial sectional view illustrating the imaging module illustrated in FIG. 20.

In the imaging unit 30c, the flat plate portion 41a of the imaging holder 41 is brought into surface contact with the incident surface 33b of the prism 33 on which the imaging device 32 and the base plate 34 are implemented, and the rodlike members 41b are brought into contact with the side surface portion 33a. Then, the contact parts are fixed. At this point in time, as illustrated in FIG. 23, part of the side surface portion 33a of the prism 33 is brought into contact with the rodlike members 41b of the imaging holder 41 for positioning. Accordingly, if the prism 33 rotates while maintaining contact with the rodlike members 41b before the contact parts are fixed, the prism 33 is held so as to maintain a state where a point C5 is located on the axis N1 (see FIG. 3). In other words, the rodlike members 41b prevent the deviation of the optical axis of the prism 33 by maintaining contact with the side surface portion 33a.

With respect to the arrangement positions of the rodlike members 41b, it is preferred that an angle θ formed by segments linking the centers of the rodlike members 41b to the point C5 is 0°<θ<180°, for example, if the center of the flat plate portion 41a is the point C5 (see FIG. 23).

According to the above-mentioned fourth embodiment, as in the first embodiment, the positions of the condensed light emission side end of the lens holder 21 and the outer periphery of the prism 33 are defined by the inner peripheral surface of the imaging holder 41 and the rodlike members 41b such that the optical axis center passing the centers of the lenses 22, 23 and 24 agrees with the point C5 being the center of the incident surface 33b of the prism 33 in the imaging module 15c. Hence, in a simple manufacturing process of simply fitting the condensed light emission side end of the lens holder 21, and the end on the incident surface 33b side of the prism 33 respectively into the openings at both ends of the imaging holder 41, it is possible to manufacture the imaging module where the optical axis center of the optical members of the lens unit 20 is caused to agree with the center of the light received by the light receiving unit 32a of the imaging device 32 of the imaging unit 30c.

Moreover, the imaging holder 41 according to the fourth embodiment can manufacture the imaging module still more easily than the above-mentioned first to third embodiments since positioning with respect to the optical axis can be performed only by bringing the prism 33 into contact with the flat plate portion 41a and the rodlike members 41b.

Figure 24:
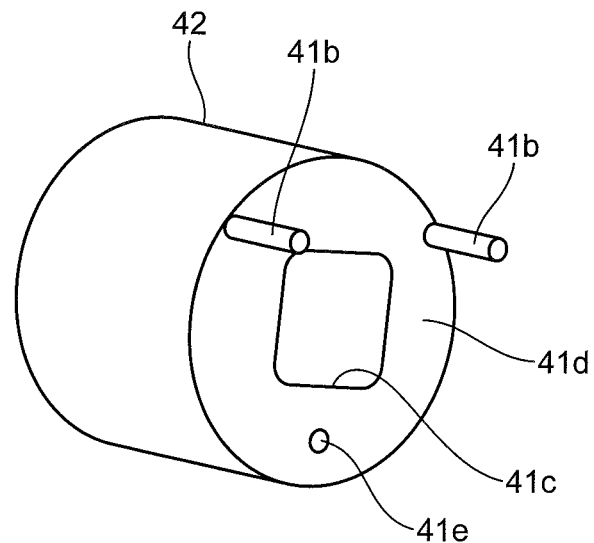
FIG. 24 is a perspective view illustrating an imaging holder of an imaging module according to a modification of the fourth embodiment of the present invention.
Figure 25:
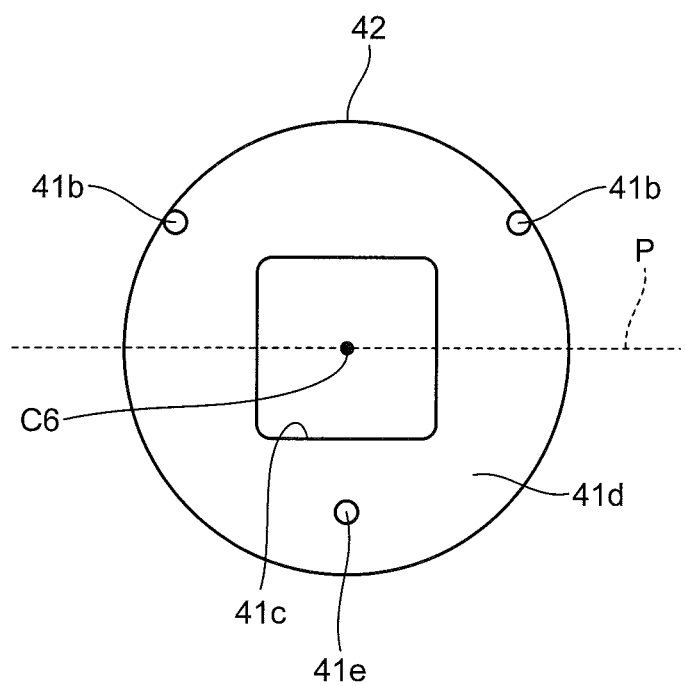
FIG. 25 is a plan view illustrating the imaging holder of the imaging module according to the modification of the fourth embodiment of the present invention.

FIG. 24 is a perspective view illustrating an imaging holder of an imaging module according to a modification of the fourth embodiment. FIG. 25 is a plan view illustrating the imaging holder of the imaging module according to the modification of the fourth embodiment. As in an imaging holder 42 according to the modification, a contact portion 41e that has a convex shape and comes into contact with the incident surface 33b may be provided on a flat plate portion 41d having a flat plate shape orthogonal to the center axis of the cylinder. Consequently, positioning with respect to the optical axis of the prism 33 can also be performed by the line contact between the rodlike members 41b and the side surface portion 33a and the point (surface) contact between the contact portion 41e and the incident surface 33b. It is preferred that the contact portion 41e be provided in a region on a side different from a region including the two rodlike members 41b within a region divided by a plane P passing a center point C6 of the flat plate portion 41d.

Moreover, in the first to fourth embodiments, an imaging unit to be mounted on a distal end section of an insertion tool of an endoscope apparatus is taken as an example for description. However, naturally, applications include electronic imaging modules in various forms from a digital camera and a digital video camera to a mobile phone with an imaging function.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging unit comprising:
a columnar prism having an outer periphery defining a circular shape when viewed from a light incident direction, the columnar prism including
an incident surface on which light is incident,
a reflecting surface for reflecting the light incident from the incident surface in a direction different from the incident surface, and
an emission surface for causing the light incident from a direction orthogonal to the incident surface and reflected from the reflecting surface to travel in a straight line and emitting the light to an outside;
an imaging sensor configured to receive the light emitted from the emission surface and perform photoelectric conversion on the light; and
a cylindrical imaging holder, protruding from at least part of an outer edge of the outer periphery of the columnar prism, for defining a position of the incident surface and holding the columnar prism,
wherein the cylindrical imaging holder having a side with an inner peripheral surface defining a cylindrical internal space having a diameter at least as large as a maximum diameter of the incident surface,
the columnar prism is coupled to the imaging device such that the incident surface is disposed in the cylindrical internal space and the emission surface contacts with the light receiving surface; and the side of the cylindrical imaging holder having a cut-out portion such that a at least a portion of the imaging sensor is arranged in the cut-out portion.

2. The imaging unit according to claim 1, wherein
the columnar prism includes a plurality of columnar prism side flat surface portions that are provided at positions on the outer periphery of the columnar prism, the positions being different from the emission surface, and that extend in a planar form in a direction in which the columnar shape extends, and the imaging holder including an opening forming the cylindrical internal space, the opening including holder side flat surfaces that are provided in line with the positions of the columnar prism side flat surface portions and form a flat surface.

3. The imaging unit according to claim 1, wherein
the columnar prism includes a plurality of recesses that are provided at positions on the outer periphery of the columnar prism, the positions being different from the emission surface, that extend in a direction in which the columnar shape extends, and that form concave shape openings toward the outside, and the imaging holder including an opening forming the cylindrical internal space, the opening including protrusions that are provided in line with the positions of the recesses and protrude in a flat plate shape allowing to be housed in internal spaces of the recesses.

4. The imaging unit according to claim 1, wherein the imaging holder includes a plurality of members protruding in a rod shape from an outer edge to a center axis direction of the imaging holder.

5. An imaging module comprising:
an imaging unit including
a columnar prism having an outer periphery defining a circular shape when viewed from a light incident direction, the columnar prism including
an incident surface on which light is incident,
a reflecting surface for reflecting the light incident from the incident surface in a direction different from the incident surface, and
an emission surface for causing the light incident from a direction orthogonal to the incident surface and reflected from the reflecting surface to travel in a straight line, and emitting the light to an outside,
an imaging sensor configured to receive the light emitted from the emission surface and perform photoelectric conversion on the light; and
a cylindrical imaging holder, protruding from at least part of an outer edge of the outer periphery of the columnar prism, for defining a position of the incident surface and holding the columnar prism;
wherein the cylindrical imaging holder having a side with an inner peripheral surface defining a cylindrical internal space having a diameter at least as large as a maximum diameter of the incident surface,
the columnar prism is coupled to the imaging device such that the incident surface is disposed in the cylindrical internal space and the emission surface contacts with the light receiving surface; and
the side of the cylindrical imaging holder having a cut-out portion such that at least a portion of the imaging sensor is arranged in the cut-out portion, and
a lens unit including
a lens for condensing light incident from one end and emitting the condensed light, and
a hollow lens holder, including openings at both ends, for holding the lens.

6. The imaging unit according to claim 1, wherein the inner peripheral surface of the cylindrical imaging holder being in contact with the outer periphery of the columnar prism.

7. The imaging module according to claim 5, wherein the inner peripheral surface of the cylindrical imaging holder being in contact with the outer periphery of the columnar prism.

* * * * *